United States Patent
Ikhlef et al.

(10) Patent No.: US 8,757,878 B2
(45) Date of Patent: Jun. 24, 2014

(54) TEMPERATURE DRIFT CORRECTION FOR MULTI-SLICE DETECTOR IN COMPUTED TOMOGRAPHY

(75) Inventors: Abdelaziz Ikhlef, Hartland, WI (US); Joseph James Lacey, Cambridge, WI (US)

(73) Assignee: General Electric Company, Schenectady, NY (US)

( * ) Notice: Subject to any disclaimer, the term of this patent is extended or adjusted under 35 U.S.C. 154(b) by 777 days.

(21) Appl. No.: 13/004,300

(22) Filed: Jan. 11, 2011

(65) Prior Publication Data

US 2012/0177174 A1 Jul. 12, 2012

(51) Int. Cl.
  G01D 18/00 (2006.01)
  A61B 6/03 (2006.01)
  H05G 1/64 (2006.01)

(52) U.S. Cl.
  USPC ........ 378/207; 378/19; 378/98.8; 250/370.09

(58) Field of Classification Search
  USPC .................................. 378/19, 98.7, 98.8, 207
  See application file for complete search history.

(56) References Cited

U.S. PATENT DOCUMENTS

| | | | |
|---|---|---|---|
| 4,967,082 A | 10/1990 | Cooke et al. | |
| 5,644,610 A * | 7/1997 | Crawford et al. | 378/19 |
| 5,867,553 A * | 2/1999 | Gordon et al. | 378/4 |
| 6,828,563 B2 | 12/2004 | Ducourant | |
| 6,980,623 B2 * | 12/2005 | Dunham et al. | 378/19 |
| 7,006,599 B2 * | 2/2006 | Okamura et al. | 378/98.11 |
| 7,102,308 B2 * | 9/2006 | Lacey et al. | 318/268 |
| 7,476,026 B2 * | 1/2009 | Braunstein | 378/207 |
| 7,772,559 B2 * | 8/2010 | Burbar et al. | 250/363.03 |
| 8,405,040 B2 * | 3/2013 | Luhta et al. | 250/370.15 |
| 8,523,434 B2 * | 9/2013 | Tsuji | 378/207 |
| 8,525,122 B2 * | 9/2013 | Chappo et al. | 250/370.11 |

* cited by examiner

*Primary Examiner* — Allen C. Ho
(74) *Attorney, Agent, or Firm* — Ziolkowski Patent Solutions Group, SC

(57) ABSTRACT

A system and method for temperature drift correction capability in a CT detector module is disclosed. A scintillator array of a CT detector module has a plurality of scintillator cells configured to detect high frequency electromagnetic energy passing through an object, with a plurality of photodiodes in a photodiode array optically coupled to the scintillator array to detect light output therefrom. A computer is provided that is programmed to measure a response of the plurality of photodiodes as a function of temperature, determine a transfer function indicative of the response of the plurality of photodiodes as a function of temperature, normalize the transfer function to a virtual operating temperature, measure a temperature of the photodiode array prior to a scan, determine a correction factor from the normalized transfer function based on the measured photodiode temperature and the virtual operating temperature, and apply the correction factor to the photodiode outputs.

20 Claims, 9 Drawing Sheets

TEMPERATURE DRIFT CORRECTION FOR MULTI-SLICE DETECTOR IN COMPUTED TOMOGRAPHY

BACKGROUND OF THE INVENTION

Embodiments of the invention relate generally to radiographic detectors for diagnostic imaging and, more particularly, to a Computed Tomography (CT) detector module configured to provide temperature drift correction capability.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector and rejecting scatter from the patient, a scintillator for converting x-rays to light energy adjacent the collimator, and photodiodes for receiving the light energy from the adjacent scintillator and producing electrical signals therefrom.

In operation, each scintillator of a scintillator array converts x-rays to light energy and discharges light energy to a photodiode adjacent thereto. Each photodiode detects the light energy and generates a corresponding electrical signal, with the strength of the electrical signal being proportional to the total energy absorbed. The outputs of the photodiodes are then transmitted to the data processing system for image reconstruction.

In order to operate in an effective manner and generate high quality and artifact free CT images, a CT detector must meet tight performance requirements. First, the detector should provide a response that is linearly related to x-ray intensity. Some of the requirements on the detector that result from this are stability of the detector over time and temperature, non-sensitivity to focal spot motion, and a bound on the light output variation over life. Furthermore, for a third generation CT scanner, the relative behavior of adjacent channels of the detector should be nearly identical in order to avoid serious ring artifacts (usually defined as channel-to-channel non-linearity variation) in reconstructed images. This variation might be affected by the scintillator behavior from one pixel to its neighbor, by the collimator plate variations, and/or by the diode pixel response. Generally, if these requirements are not met, ring artifacts, bands and/or smudges/spots might appear in images.

One of the contributors of this channel-to-channel variation (or module to module variation) is the gain variation caused between detector pixels (composed of the collimator-scintillator-photodiode arrangement) due to the variation of temperature. In Volume CT, the variation of the temperature at the pixels will be high and tight thermal control from calibration conditions to scanning conditions is typically required. The thermal gain temperature coefficient drift in the detector module may have multiple root causes, including the diode, collimator, scintillator, and DAS electronics. To overcome this problem, very tight thermal control can be introduced on the detector or, alternatively, the thermal drift can be compensated for by introducing a thermal calibration or correction.

Therefore, it would be desirable to design a CT detector that minimizes gain variation between detector pixels resulting from temperature variation. It would also be desirable for such a CT detector to minimize such gain variation by providing a thermal calibration or correction to compensate for such temperature variation.

BRIEF DESCRIPTION OF THE INVENTION

The invention is a directed apparatus for CT image acquisition that provides for temperature drift correction capability.

In accordance with one aspect of the invention, a CT system includes a rotatable gantry having an opening to receive an object to be scanned, a high frequency electromagnetic energy projection source configured to project a high frequency electromagnetic energy beam toward the object, and a scintillator array having a plurality of scintillator cells wherein each cell is configured to detect high frequency electromagnetic energy passing through the object, and a photodiode array optically coupled to the scintillator array and comprising a plurality of photodiodes configured to detect light output from a corresponding scintillator cell. The CT system also includes a data acquisition system (DAS) connected to the photodiode array and configured to receive the photodiode outputs and an image reconstructor connected to the DAS and configured to reconstruct an image of the object from the photodiode outputs received by the DAS. The CT system further includes a computer programmed to measure a response of the plurality of photodiodes as a function of temperature, determine a transfer function indicative of the response of the plurality of photodiodes as a function of temperature, and normalize the transfer function to a virtual operating temperature. The computer is also programmed to measure a temperature of the photodiode array prior to a scan, determine a correction factor from the normalized transfer function based on the measured photodiode temperature and the virtual operating temperature, and apply the correction factor to the photodiode outputs.

In accordance with another aspect of the invention, a method for correcting temperature drift in a CT detector module having a plurality of detector pixels that form a plurality of detector channels includes measuring a gain of a plurality of detector pixels in the detector module as a function of temperature during a detector module calibration and determining a transfer function indicative of the gain of the plurality of detector pixels as a function of temperature. The method also includes normalizing the transfer function to a virtual operating temperature, measuring a temperature of the plurality of detector pixels prior to performing a imaging scan with the CT system, and performing the imaging scan with the CT system to acquire image data from each of the plurality of detector pixels. The method further includes determining a correction factor to be applied to the acquired image data, the correction factor being determined from the normalized transfer function based on the measured photodiode temperature and the virtual operating temperature and applying the correction factor to the acquired image data so as to adjust a gain of each of the plurality of detector pixels to account for a temperature variation between the detector module calibration temperature and the temperature of the plurality of detector pixels measured prior to performing the scan.

In accordance with yet another aspect of the invention, a non-transitory computer readable storage medium has stored thereon a computer program comprising instructions, which when executed by a computer, cause the computer to measure a gain change of a plurality of photodiode pixels in a CT detector module as a function of temperature during a detector calibration and determine a transfer function indicative of the gain of the plurality of photodiode pixels as a function of temperature. The instructions also cause the computer to normalize the transfer function to a virtual operating temperature and measure a temperature of the plurality of photodiode pixels prior to or during an imaging scan that acquires CT data. The instructions further cause the computer to determine a thermal correction from the normalized transfer function based on the measured photodiode pixel temperatures and the virtual operating temperature and apply the thermal correction to the CT data so as to make a correction of thermal drift from a temperature of the detector module during detector calibration to a temperature of the detector module prior to or during the imaging scan.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations, such as configurations extending up to 256 slices and beyond or below. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 1:
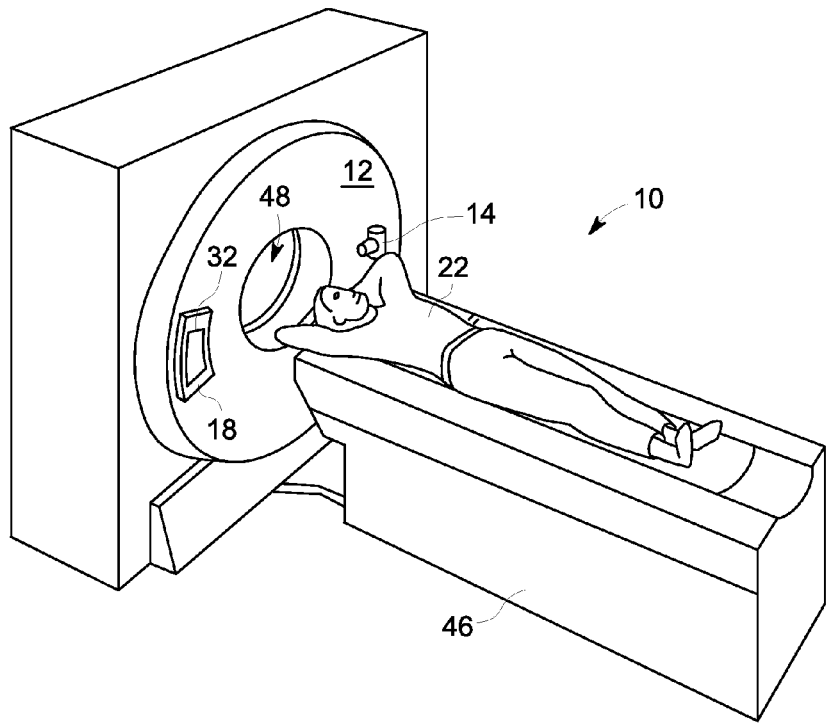
FIG. 1 is a pictorial view of a CT imaging system.
Figure 2:
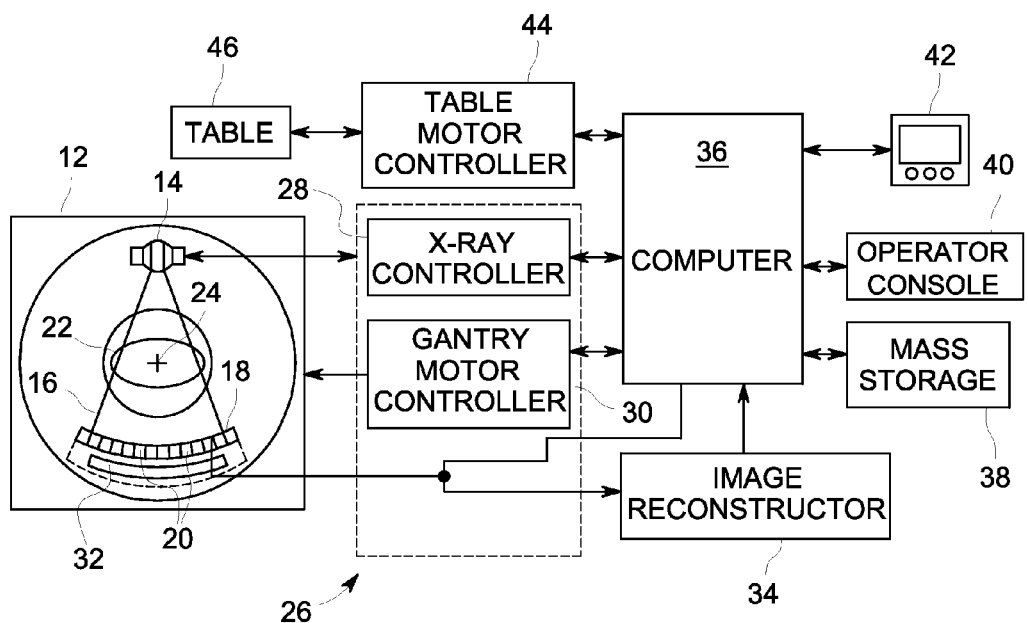
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays toward a detector assembly 18 on the opposite side of the gantry 12. Referring now to FIG. 2, detector assembly 18 is formed by a plurality of detector modules 20 and data acquisition systems (DAS) 32. The plurality of detector modules 20 sense the projected x-rays 16 that pass through a medical patient 22, and DAS 32 converts the data to digital signals for subsequent processing. Each detector module 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
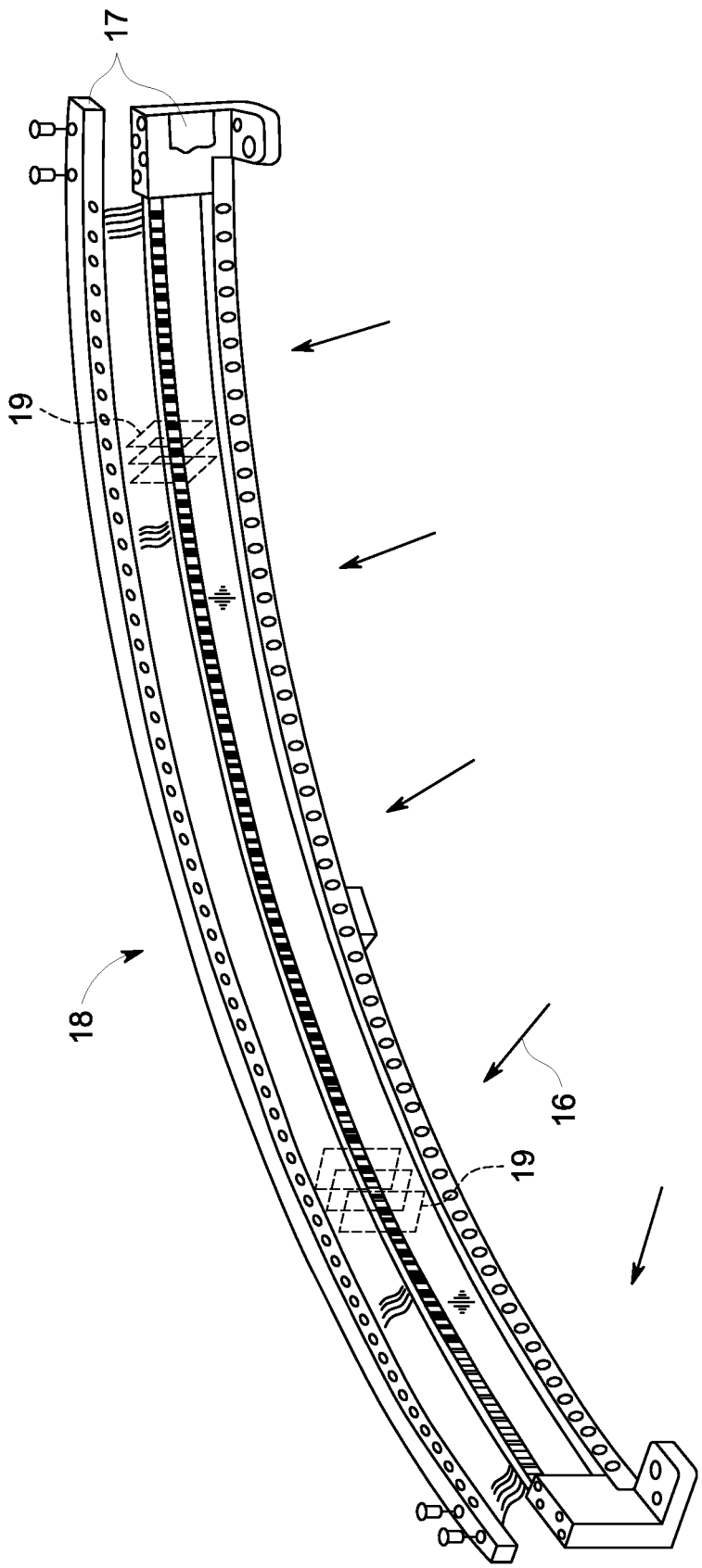
FIG. 3 is a perspective view of one embodiment of a CT system detector array.
Figure 4:
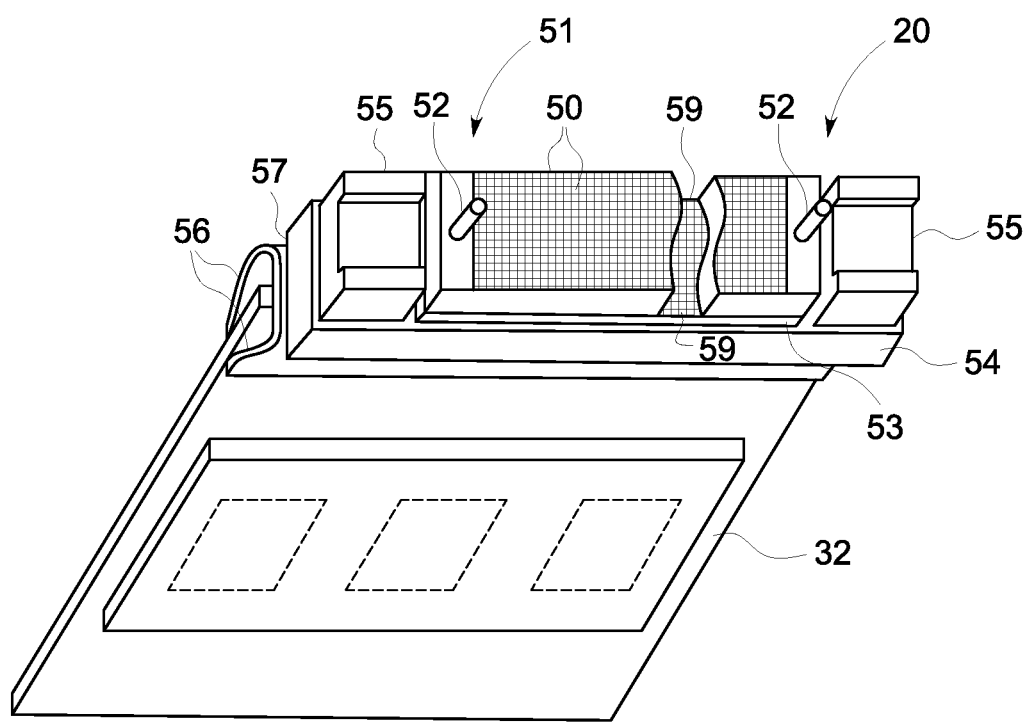
FIG. 4 is a perspective view of a CT detector module according to an embodiment of the invention.
Figure 5:
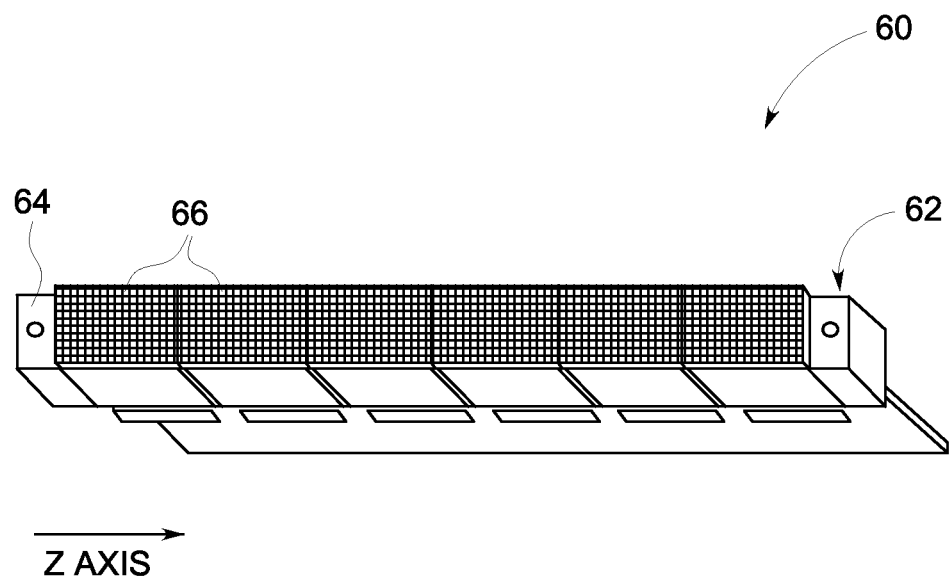
FIG. 5 is a perspective view of a CT detector module according to another embodiment of the invention.

As shown in FIG. 3, detector assembly 18 includes rails 17 having collimating blades or plates 19 placed there between. Plates 19 are positioned to collimate x-rays 16 before such beams impinge upon, for instance, detector module 20 of FIG. 4 or detector module 60 of FIG. 5, positioned on detector assembly 18. In the embodiment of FIG. 4, detector assembly 18 includes 57 detectors 20, each detector module 20 having an array size of 64×16 of detector elements 50. As a result, detector assembly 18 has 64 rows and 912 columns (16×57 detectors), which allows 64 simultaneous slices of data to be collected with each rotation of gantry 12 across a plurality of detector channels. In the embodiment of FIG. 5, detector assembly 18 includes 57 detector modules 60, each detector module 60 having an array size of 256×16 of pixel elements. As a result, detector assembly 18 has 256 rows and 912 columns (16×57 detectors), which allows 256 simultaneous slices of data to be collected with each rotation of gantry 12.

Referring to FIG. 4, according to one embodiment, detector module 20 includes DAS 32, with each detector module 20 including a number of detector elements 50 arranged in pack 51. Detector modules 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detector modules 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

Referring to FIG. 5, according to another embodiment, a detector module 60 is provided that includes a module frame 62 having a top surface 64 thereon. According to embodiments of the invention, top surface 64 can be constructed as a flat surface or, alternatively, to have a stepped configuration with a plurality of facets thereon. As shown in FIG. 5, a plurality of detector sub-modules 66 or "nano-modules" are positioned onto top surface of module frame 62 to receive and process x-rays that attenuate through a patient or object. According to embodiments of the invention, the number of sub-modules 66 positioned on top surface 64 of module frame 62 can be controlled during a manufacturing process based on the operating requirements of detector modules 60 in the CT system 10 (FIG. 1). That is, the sub-modules 66 of detector module 60 are configured as tileable sub-modules, in that sub-modules 66 can be selectively added to module frame 62 as desired such that the number of sub-modules 66 included in detector module 60 can be controlled, so as to vary the amount of coverage along the Z-axis (i.e., vary/control the number of slices acquired). Thus, based on a populating and depopulating of sub-modules 66 on module frame 62, it is recognized that a detector module 60 can be built having a controllable length/coverage along the Z-axis.

Figure 6:
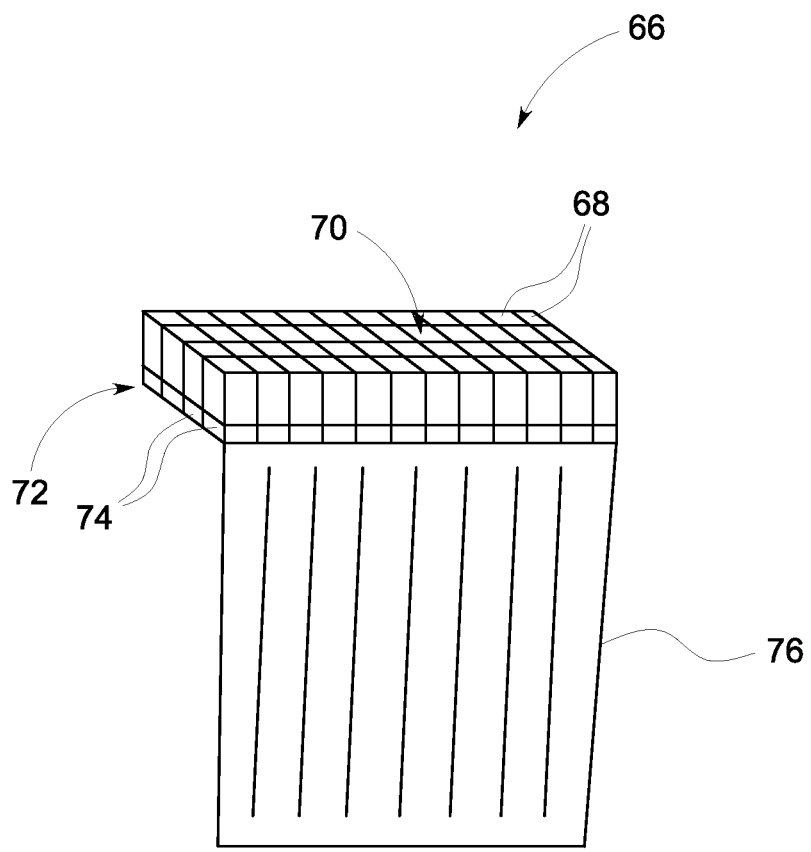
FIG. 6 is a perspective view of a detector sub-module for use with the detector module of FIG. 5 according to an embodiment of the invention

A detailed view of a sub-module 66 is shown in FIG. 6 according to an embodiment of the invention. Sub-module 66 includes a number of scintillator detector elements or pixels 68 are arranged to form a scintillating pack array 70. For example, a scintillating pack array 70 may be composed of a 32×16 array of scintillator detector elements 68, such that each scintillating pack array 70 includes 32 slices and 16 channels. The scintillating pack array 70 is positioned on a backlit diode array 72 formed of a plurality of diode elements or pixels 74 (i.e., a 32×16 array of diodes). Backlit diode array 72 is in turn electrically coupled to a flex circuit 76 that is attached to a face of the backlit diode array 72. In the operation of one embodiment, x-rays impinge within scintillator detector elements 68 to generate photons that traverse pack array 70 to backlit diode array 72, with each photon being detected on a diode element 74 within backlit diode array 72. The backlit diode array 72 thereby generates signals that are carried from backlit diode array 72, through flex circuit 76.

It is recognized that detector module 20, 60, in receiving x-rays attenuated by patient 22 and converting those x-rays to photons and corresponding electrical charges, must meet tight performance requirements with respect to gain variation between detector elements (composed of the collimator-scintillator-photodiode arrangement) that is due to the temperature variations. In order to avoid temperature induced artifacts in resulting images that might result from such gain variation, any such temperature variations in the detector module that occur during operation thereof (i.e., during image acquisition) must be accounted for. According to embodiments of the invention, such thermal correction can be achieved by way of a temperature drift correction technique or algorithm applied by the CT system 10 (FIG. 1).

Figure 7:
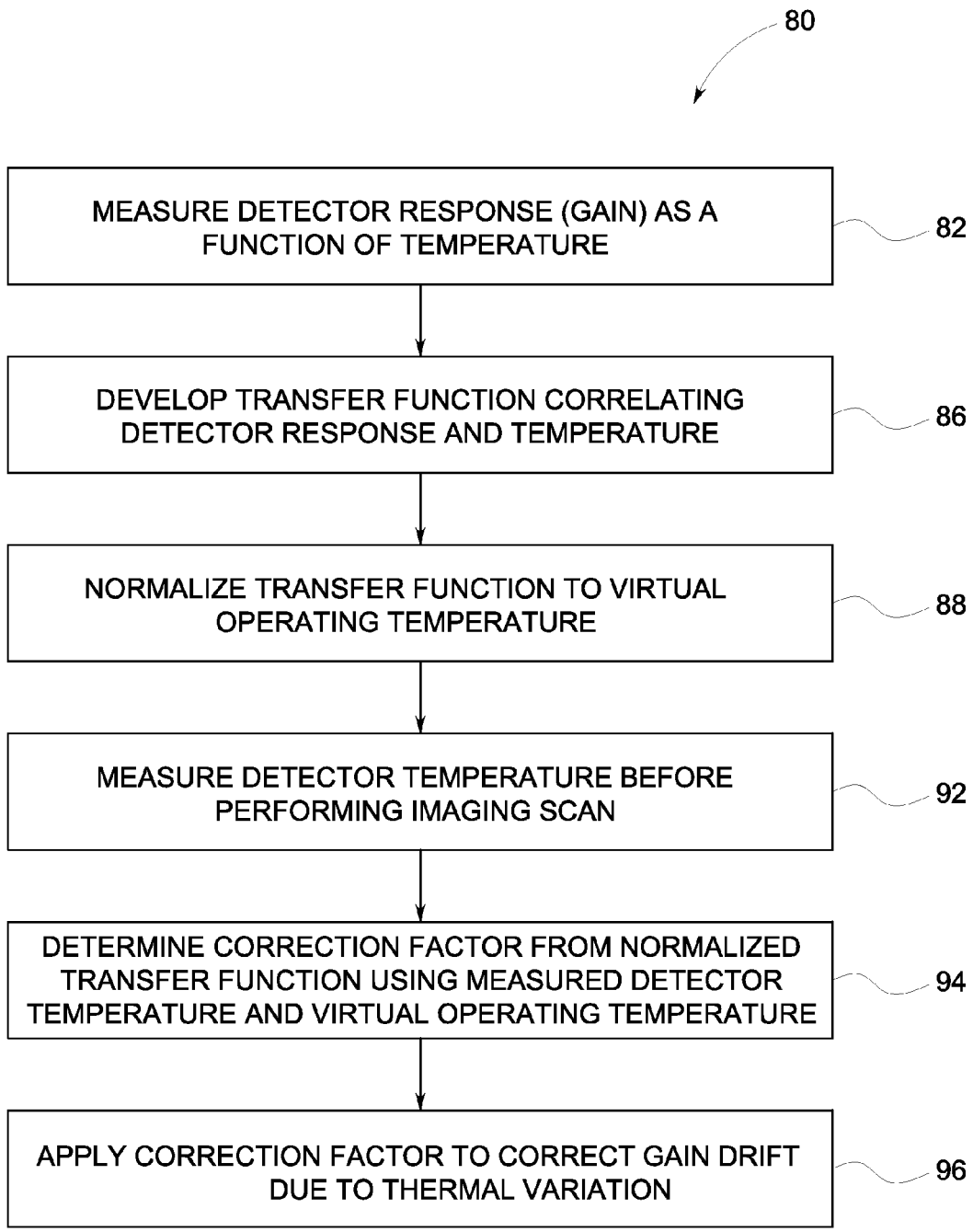
FIG. 7 is a flowchart illustrating a technique for temperature drift correction in a CT detector module according to an embodiment of the invention.
Figure 8:
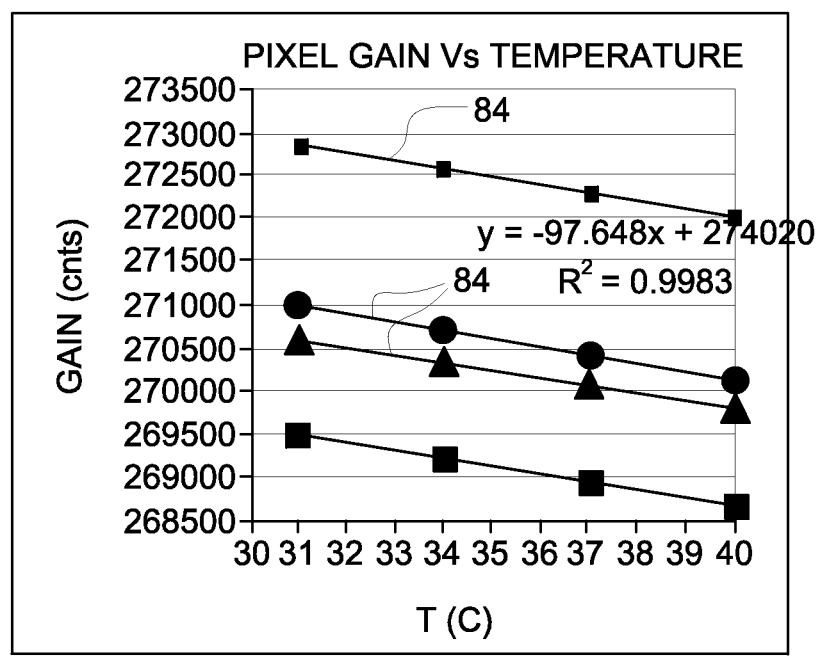
FIG. 8 is a graph illustrating detector pixel gain as a function of temperature.

Referring now to FIG. 7, a computer-implemented technique 80 for thermal correction is illustrated according to an embodiment of the invention. Technique 80 can be performed by computer 36 or DAS 32 (FIG. 1), for example, or by another separate computer processing unit coupled to CT system 10, according to embodiments of the invention. As shown in FIG. 7, technique 80 begins with measuring the detector response, i.e., gain from an x-ray signal, as a function of temperature at block 82. The measurement of the detector response can be performed, for example, during calibration of the detector module in a pretest bay, at typical detector calibration temperatures. According to an exemplary embodiment, a response for each pixel of the detector is measured as a function of temperature, so as to provide for individualized gain versus temperature response for each pixel. An example of such a measured detector response is illustrated in FIG. 8, where gain as a function of temperature is measured for each of a plurality of pixels, with a small sample of four pixels 84 being illustrated.

Referring again to FIG. 7, in a next step of technique 80, a transfer function is developed at block 86 that correlates the detector response (i.e., pixel gain) to temperature variation. This transfer function can be a first or second order depending on the nature of the detector. According to an exemplary embodiment, a transfer function is developed to determine the gain for each channel, with the gain G being described according to:

$$G(ch,T)=G(ch,T_0)\cdot[1+K_1(T_1-T_0)+K_2(T_1-T_0)^2+\ldots] \quad [\text{Eqn. 1}],$$

where $K_1$ and $K_2$ are gain-temperature coefficients of the detector response to x-rays for each channel and T and $T_0$ are the temperatures measured for each detector channel or detector module. For a second order transfer function, two coefficients (i.e., $K_1$ and $K_2$) for each channel are provided that can be referenced, such as via accessing a look-up table, that correlate the detector response with temperature variation. The transfer function of [Eqn. 1] thus provides for generation of calibration vectors for each detector/photodiode pixel in the detector module that are illustrative of gain response as a function of temperature. According to an exemplary embodiment, the calibration vectors can be stored in a look-up table (i.e., calibration vector table) for future access.

It is recognized that the transfer function shown in [Eqn. 1] can be represented differently for each channel of the detector module 20 by choosing a virtual operating temperature (i.e., global reference) to which every channel is normalized. Thus, in a next step of technique 80, the transfer function of [Eqn. 1] is normalized to a selected virtual operating temperature at block 88. Upon such normalization, the gain change scaling factor $K(ch,T_{scan})$ can be represented as follows:

$$K(ch,T_{scan})=[1+K_1(T_{scan}-T_{oper})+K_2(T_{scan}-T_{oper})^2+\ldots] \quad [\text{Eqn. 2}],$$

where $T_{oper}$ is the selected virtual operating temperature for a detector channel and $T_{scan}$ is the temperature measured for a detector channel, such as a temperature measured during operation of the detector. It is also recognized, however, that $T_{scan}$ could be the temperature measured for a detector channel during any scan performed by the detector.

Figure 9:
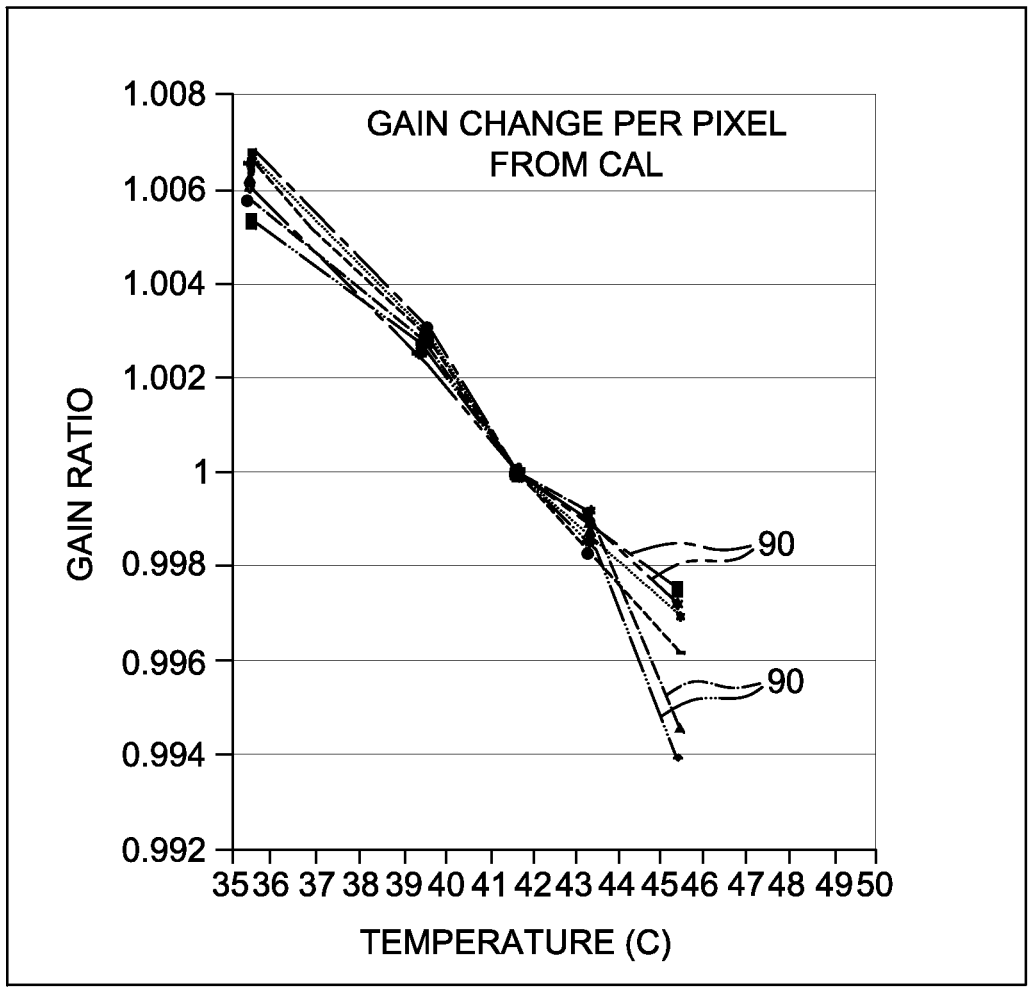
FIG. 9 is a graph illustrating gain change per detector pixel from calibration.

Based on the implementation of the normalized transfer function of [Eqn. 2] for the selected virtual operating temperature, gain response for each detector pixel from calibration temperature to scanning temperature can be determined. Referring to FIG. 9, an example of a gain ratio per pixel from calibration temperature to the virtual operating temperature is shown for a selected virtual operating temperature, $T_{oper}$=41.3° C., with gain change 90 being shown for multiple pixels.

An example of normalizing the transfer function of [Eqn. 2] for a selected virtual operating temperature is provided below in [Eqn. 3], where if the detector temperature range is between, 35° C. and 43° C., a temperature of 39° C. can be chosen as the virtual operating temperature. For a virtual operating temperature of 39° C., the normalized transfer function of [Eqn. 2] is thus represented by:

$$G(ch,T_{39C})=G(ch,T_{scan})\cdot K((ch,T_{scan}) \quad [\text{Eqn. 3}].$$

Every scan (calibration or imaging) is corrected to 39° C. according to [Eqn. 3], and the term $[1+K_1(T_{scan}-T_{39C})+K_2(T_{scan}-T_{39C})^2+\ldots]$ is the correction scaling factor to simulate the gain at 39° C.

In applying the correction factor determined via [Eqn. 3] to an imaging scan to be performed, it is recognized that it is necessary to know a temperature, $T_{scan}$, at which that scan is performed. Thus, referring again to FIG. 7, in a next step of technique 80 the temperature at every channel is measured before each scan at block 92, with the temperature, $T_{scan}$, being measured by way of a thermistor or a reverse biasing of the photodiodes, for example. Upon measurement of the temperature at each channel, the correction factor is determined at block 94 based on the input of the measured detector channel temperature and the virtual operating temperature into the transfer function of [Eqn. 3]. The correction factor is then applied at block 96 (after offset correction), providing for implementing of the correction of the gain response as a function of the temperature so as to compensate for the gain drift due to temperature/thermal variation in the CT image data acquired during the scan.

Thus, beneficially, the creation of calibration vectors for each pixel provided by technique 80 allows for a relaxation of the thermal management control in the detector, which is already tight, to a much larger range of +/−5 C.° (i.e., a range of 10 C.°, for example. Additionally, creation of calibration vectors for each pixel provided by technique 80 allows for a relaxation of the requirements of the detector channel (i.e., scintillator-diode-ASIC), which will be used to compensate for the gain drift due to temperature drift. Implementation of technique 80 also reduces the time required to warm-up the detector, improves image quality.

While technique 80 is described above as providing for the determination of correction factors for each channel in a detector module, it is recognized that a correction factor could also/only be determined for each individual detector module (and not at the channel level). The determination/implementation of correction factors either at the channel level or at the detector module level can be based on the accuracy required in calibrating the detector module.

Figure 10:
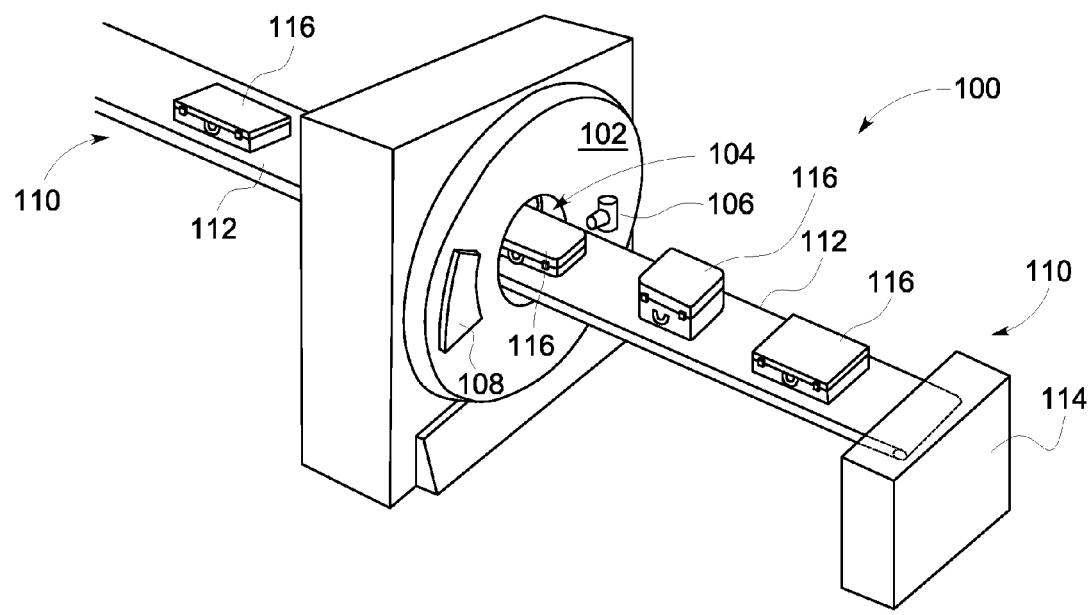
FIG. 10 is a pictorial view of a CT system for use with a non-invasive package inspection system.

Referring now to FIG. 10, a package/baggage inspection system 100 is shown that includes a rotatable gantry 102 having an opening 104 therein through which packages or pieces of baggage may pass, according to an embodiment of the invention. The rotatable gantry 102 houses a high frequency electromagnetic energy source 106 as well as a detector assembly 108 having detector modules 20, 60 similar to that shown in FIGS. 4 and 5. A conveyor system 110 is also provided and includes a conveyor belt 112 supported by structure 114 to automatically and continuously pass packages or baggage pieces 116 through opening 104 to be scanned. Packages or baggage pieces 116 are fed through opening 104 by conveyor belt 112, imaging data is then acquired, and the conveyor belt 112 removes the packages or baggage pieces 116 from opening 104 in a controlled and continuous manner. As a result, postal inspectors, baggage handlers, and other security personnel may non-invasively inspect the contents of packages or baggage pieces 116 for explosives, knives, guns, contraband, etc.

Therefore, according to one embodiment of the invention, a CT system includes a rotatable gantry having an opening to receive an object to be scanned, a high frequency electromagnetic energy projection source configured to project a high frequency electromagnetic energy beam toward the object, and a scintillator array having a plurality of scintillator cells wherein each cell is configured to detect high frequency electromagnetic energy passing through the object, and a photodiode array optically coupled to the scintillator array and comprising a plurality of photodiodes configured to detect light output from a corresponding scintillator cell. The CT system also includes a data acquisition system (DAS) connected to the photodiode array and configured to receive the photodiode outputs and an image reconstructor connected to the DAS and configured to reconstruct an image of the object from the photodiode outputs received by the DAS. The CT system further includes a computer programmed to measure a response of the plurality of photodiodes as a function of temperature, determine a transfer function indicative of the response of the plurality of photodiodes as a function of temperature, and normalize the transfer function to a virtual operating temperature. The computer is also programmed to measure a temperature of the photodiode array prior to a scan, determine a correction factor from the normalized transfer function based on the measured photodiode temperature and the virtual operating temperature, and apply the correction factor to the photodiode outputs.

According to another embodiment of the invention, a method for correcting temperature drift in a CT detector module having a plurality of detector pixels that form a plurality of detector channels includes measuring a gain of a plurality of detector pixels in the detector module as a function of temperature during a detector module calibration and determining a transfer function indicative of the gain of the plurality of detector pixels as a function of temperature. The method also includes normalizing the transfer function to a virtual operating temperature, measuring a temperature of the plurality of detector pixels prior to performing a imaging scan with the CT system, and performing the imaging scan with the CT system to acquire image data from each of the plurality of detector pixels. The method further includes determining a correction factor to be applied to the acquired image data, the correction factor being determined from the normalized transfer function based on the measured photodiode temperature and the virtual operating temperature and applying the correction factor to the acquired image data so as to adjust a gain of each of the plurality of detector pixels to account for a temperature variation between the detector module calibration temperature and the temperature of the plurality of detector pixels measured prior to performing the scan.

According to yet another embodiment of the invention, a non-transitory computer readable storage medium has stored thereon a computer program comprising instructions, which when executed by a computer, cause the computer to measure a gain change of a plurality of photodiode pixels in a CT detector module as a function of temperature during a detector calibration and determine a transfer function indicative of the gain of the plurality of photodiode pixels as a function of temperature. The instructions also cause the computer to normalize the transfer function to a virtual operating temperature and measure a temperature of the plurality of photodiode pixels prior to or during an imaging scan that acquires CT data. The instructions further cause the computer to determine a thermal correction from the normalized transfer function based on the measured photodiode pixel temperatures and the virtual operating temperature and apply the thermal correction to the CT data so as to make a correction of thermal drift from a temperature of the detector module during detector calibration to a temperature of the detector module prior to or during the imaging scan.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A CT system comprising:
a rotatable gantry having an opening to receive an object to be scanned;
a high frequency electromagnetic energy projection source configured to project a high frequency electromagnetic energy beam toward the object;
a scintillator array having a plurality of scintillator cells, wherein each scintillator cell is configured to detect high frequency electromagnetic energy passing through the object;
a photodiode array optically coupled to the scintillator array and comprising a plurality of photodiodes configured to detect light output from a corresponding scintillator cell;
a data acquisition system (DAS) connected to the photodiode array and configured to receive outputs from the plurality of photodiodes;
an image reconstructor connected to the DAS and configured to reconstruct an image of the object from the outputs from the plurality of photodiodes received by the DAS; and
a computer programmed to:
measure a response of the plurality of photodiodes as a function of temperature;
determine a transfer function indicative of the response of the plurality of photodiodes as a function of temperature;
normalize the transfer function to a virtual operating temperature;
measure a temperature of the photodiode array prior to a scan;
determine a correction factor from the normalized transfer function based on the measured photodiode array temperature and the virtual operating temperature; and
apply the correction factor to the outputs from the plurality of photodiodes.

2. The CT system of claim 1 wherein the response of the plurality of photodiodes comprises a gain.

3. The CT system of claim 1 wherein the computer is further programmed to measure a temperature of each of a plurality of channels of the photodiode array prior to a scan.

4. The CT system of claim 3 wherein the computer is further programmed to apply the correction factor to each of the plurality of channels of the photodiode array.

5. The CT system of claim 4 wherein the computer is further programmed to generate the transfer function according to:

$$K(ch, T_{scan}) = [1 + K_1(T_{scan} - T_{oper}) + K_2(T_{scan} - T_{oper})^2 + \ldots]$$

where $K(ch, T_{scan})$ is a gain change scaling factor of a channel of the photodiode array, $K_1$ and $K_2$ are gain-temperature coefficients of a response to x-rays for a channel, $T_{oper}$ is a virtual operating temperature for a channel, and $T_{scan}$ is a channel temperature.

6. The CT system of claim 5 wherein the computer is further programmed to store the $K_1$ and $K_2$ gain-temperature coefficients in a look-up table.

7. The CT system of claim 6 wherein the computer is further programmed to generate a calibration vector table based on the transfer function, the calibration vector table including calibration vectors therein for each of the plurality of photodiodes.

8. The CT system of claim 1 wherein the computer is further programmed to set a thermal management control for the photodiode array from calibration conditions to scanning conditions to a range of approximately 10° C.

9. The CT system of claim 1 further comprising a thermistor, and wherein the computer is further programmed to measure the temperature of the photodiode array prior to a scan via one of the thermistor and a reverse biasing of the plurality of photodiodes.

10. The CT system of claim 1 wherein the correction factor is configured to make a correction of thermal drift from a calibration temperature of the photodiode array to an imaging scan temperature of the photodiode array.

11. A method for correcting temperature drift in a CT detector module having a plurality of detector pixels that form a plurality of detector channels, the method comprising:
measuring a gain of a plurality of detector pixels in the CT detector module as a function of temperature during a CT detector module calibration;
determining a transfer function indicative of a gain of the plurality of detector pixels as a function of temperature;
normalizing the transfer function to a virtual operating temperature;
measuring a temperature of the plurality of detector pixels prior to performing an imaging scan with a CT system;
performing the imaging scan with the CT system to acquire image data from each of the plurality of detector pixels;
determining a correction factor to be applied to the acquired image data, the correction factor being determined from the normalized transfer function based on the measured temperature of the plurality of detector pixels and the virtual operating temperature; and
applying the correction factor to the acquired image data so as to adjust a gain of each of the plurality of detector pixels to account for a temperature variation between a temperature of the CT detector module during calibration and the temperature of the plurality of detector pixels measured prior to performing the imaging scan.

12. The method of claim 11 wherein measuring the temperature of the plurality of detector pixels comprises measuring the temperature of each of the plurality of detector channels in the CT detector module prior to an image scan.

13. The method of claim 12 wherein the normalized transfer function is set forth as:

$$K(ch, T_{scan}) = [1 + K_1(T_{scan} - T_{oper}) + K_2(T_{scan} - T_{oper})^2 + \ldots]$$

where $K(ch, T_{scan})$ is a gain change scaling factor of a detector channel, $K_1$ and $K_2$ are gain-temperature coefficients of the CT detector module response to x-rays for a detector channel, $T_{oper}$ is the virtual operating temperature for a detector channel, and $T_{scan}$ is the temperature measured for a detector channel.

14. The method of claim 11 wherein determining the correction factor comprises determining a correction factor for each of the plurality of detector channels of the CT detector module.

15. The method of claim 11 further comprising generating calibration vectors for each of the plurality of detector pixels in the CT detector module representative of gain change as a function of temperature.

16. The method of claim 15 wherein generating a calibration vector for each of the plurality of detector pixels comprises accessing a look-up vector table having calibration vectors for each of the plurality of detector pixels stored therein.

17. The method of claim 11 wherein the correction factor is configured to make a correction of thermal drift from a temperature of the CT detector module during calibration to a temperature of the CT detector module during the imaging scan.

18. A non-transitory computer readable storage medium having stored thereon a computer program comprising instructions, which when executed by a computer, cause the computer to:
measure a gain change of a plurality of photodiode pixels in a CT detector module as a function of temperature during a detector calibration;
determine a transfer function indicative of the gain change of the plurality of photodiode pixels as a function of temperature;
normalize the transfer function to a virtual operating temperature;
measure a temperature of the plurality of photodiode pixels prior to or during an imaging scan that acquires CT data;
determine a thermal correction from the normalized transfer function based on the measured temperature of the plurality of photodiode pixels and the virtual operating temperature; and
apply the thermal correction to the CT data so as to make a correction of thermal drift from a temperature of the plurality of photodiode pixels during detector calibration to a temperature of the plurality of photodiode pixels prior to or during the imaging scan.

19. The non-transitory computer readable storage medium of claim 18 having further instructions that cause the computer to:
generate calibration vectors for each of the plurality of photodiode pixels in the CT detector module representative of gain change as a function of temperature; and
generate a look-up vector table having the calibration vectors for each of the plurality of photodiode pixels stored therein.

20. The non-transitory computer readable storage medium of claim 18 having further instructions that cause the computer to measure a temperature of each of a plurality of channels of the plurality of photodiode pixels prior to an imaging scan; and
wherein the instructions that cause the computer to determine the transfer function cause the computer to determine the transfer function according to:

$$K(ch, T_{scan}) = [1 + K_1(T_{scan} - T_{oper}) + K_2(T_{scan} - T_{oper})^2 + \ldots]$$

where $K(ch, T_{scan})$ is a gain change scaling factor of a channel, $K_1$ and $K_2$ are gain-temperature coefficients a response to x-rays for a channel, $T_{oper}$ is the virtual operating temperature for a channel, and $T_{scan}$ is the temperature measured for a channel.

* * * * *